US010584818B2

(12) United States Patent
Blake et al.

(10) Patent No.: US 10,584,818 B2
(45) Date of Patent: Mar. 10, 2020

(54) FLUID CONNECTOR WITH CLAMP AND PROTECTION (71) Applicant: SARTORIUS STEDIM FMT SAS, Aubagne (FR)

(72) Inventors: Florian Blake, Hyeres (FR); Jeremy Gibelin, Le Beausset (FR); Isabelle Gay, Peypin (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 911 days.

(21) Appl. No.: 14/901,524

(22) PCT Filed: Jun. 24, 2014

(86) PCT No.: PCT/FR2014/051579
§ 371 (c)(1),
(2) Date: Dec. 28, 2015

(87) PCT Pub. No.: WO2014/207370
PCT Pub. Date: Dec. 31, 2014

(65) Prior Publication Data
US 2016/0146386 A1 May 26, 2016

(30) Foreign Application Priority Data

Jun. 28, 2013 (FR) .................................... 13 56351

(51) Int. Cl.
*F16L 37/08* (2006.01)
*A61M 39/10* (2006.01)
(Continued)

(52) U.S. Cl.
CPC .......... *F16L 37/08* (2013.01); *A61M 39/1011* (2013.01); *A61M 39/12* (2013.01);
(Continued)

(58) Field of Classification Search
CPC . F16L 37/08; F16L 57/00; F16L 33/02; F16L 33/025; F16L 33/227;
(Continued)

(56) References Cited

U.S. PATENT DOCUMENTS 4,049,034 A  9/1977 Vcelka et al.
4,340,052 A * 7/1982 Dennehey .......... A61M 39/1011
                                                        604/317
(Continued)

FOREIGN PATENT DOCUMENTS

DE  20 2009 000508   4/2009
EP     2 143 986    1/2010
(Continued)

OTHER PUBLICATIONS

International Search Report dated Oct. 27, 2014, corresponding to PCT/FR2014/051579.

*Primary Examiner* — David Bochna
*Assistant Examiner* — James A Linford
(74) *Attorney, Agent, or Firm* — Young & Thompson (57) ABSTRACT Disclosed is a fluid-connection device for connecting a first wall defining a first fluid space, in the form of a flexible pipe, to a second wall defining a second fluid space, in the form of a flexible or rigid disposable pipe or enclosure, in a biopharmaceutical assembly, including a first connector in fluid communication with the first space, the first connector including a tubular nozzle for receiving the pipe by insertion along the axis A, a pipe clamp arranged around the end of the pipe in order to clamp the pipe onto the tubular nozzle of the first connector, a protective cover forming a separate part, capable of being snap-fit in an operative position in which the cover is at least partially surrounding the first (Continued)

connector and the pipe clamp thereof, by way of which the pipe clamp cannot come into direct contact with external elements.

15 Claims, 3 Drawing Sheets

(51) Int. Cl.
    *F16L 33/22*     (2006.01)
    *F16L 37/098*     (2006.01)
    *F16L 33/025*     (2006.01)
    *A61M 39/12*     (2006.01)
    *F16L 33/02*     (2006.01)
    *F16L 57/00*     (2006.01)
    *A61J 1/14*     (2006.01)

(52) U.S. Cl.
    CPC ............. *F16L 33/02* (2013.01); *F16L 33/025* (2013.01); *F16L 33/227* (2013.01); *F16L 37/0987* (2013.01); *F16L 57/00* (2013.01); *A61J 1/1481* (2015.05); *A61M 2039/1027* (2013.01); *A61M 2039/1066* (2013.01); *F16L 2201/10* (2013.01); *F16L 2201/44* (2013.01)

(58) Field of Classification Search
    CPC ............... F16L 37/0987; F16L 2201/10; F16L 2201/44; A61M 39/1011; A61M 39/12; A61M 2039/1027; A61M 2039/1066; A61J 1/1481
    See application file for complete search history.

(56) References Cited

U.S. PATENT DOCUMENTS

| | | |
|---|---|---|
| 8,220,837 B2 | 7/2012 | Kaneda |
| 2010/0148497 A1 | 6/2010 | Kaneda |
| 2011/0163537 A1 | 7/2011 | Baggenstos |

FOREIGN PATENT DOCUMENTS

| | | |
|---|---|---|
| EP | 2 341 273 | 7/2011 |
| EP | 2 497 989 | 9/2012 |
| FR | 2 385 971 | 10/1978 |
| WO | 03/074918 | 9/2003 |

* cited by examiner

FLUID CONNECTOR WITH CLAMP AND PROTECTION

FIELD OF THE INVENTION

The invention relates to fluid connectors, in particular for fluid connections to couple a fluid-conveying pipe to another pipe or to a container, in the field of biopharmaceutical applications.

BACKGROUND OF THE INVENTION

Specifically, the tubes or pipes used in the biopharmaceutical field are flexible or highly flexible pipes which are used to convey various biopharmaceutical substances, most often with the aseptic precautions required.

In biopharmaceutical applications, this type of flexible pipe allows the circulation, passage, and communication of a fluid such as a biopharmaceutical fluid, and can either be connected to a similar flexible pipe or to a vessel or container which may be flexible or rigid.

The vessel or container in question may in this case be a container for storing and/or processing content such as a biopharmaceutical product. Such a container is in this case understood to mean a rigid or semi-rigid reusable container or a flexible disposable container such as a bag or possibly even a filter cartridge.

This bag may be one of the substantially thin "2D" bags, such as those marketed by Sartorius Stedim Biotech under the brand Flexboy®, having a typical volume of between 50 ml and 50 liters. This flexible bag may also be a "3D" bag, such as those marketed by Sartorius Stedim Biotech under the brand Flexel®, having a larger volume and a substantial size in all three dimensions. Note that a pipe such as the pipe of the invention can be placed between two bags or a larger number of bags.

A pipe of the invention, usually of circular cross-section, is typically made of a plastic such as silicone, thermoplastic elastomers (TPE), or PVC, although this list is not limiting. It has a certain general stability, and simultaneously both a certain overall flexibility and a certain local flexibility, which allows crimping the pipe or substantially deforming it radially when sufficient force is applied.

In a typical embodiment, for example, the pipe has an outer diameter between 8 mm and 30 mm for example, with the thickness depending on the material, the diameter, and the applications.

In the prior art, in order to couple such a flexible pipe, it is slipped over a tubular nozzle, whereupon a pipe clamp is placed around the pipe and the clamp is then tightened. The tightened clamp thus exerts a radial inward pressure to retain the flexible pipe on the nozzle, on the one hand to ensure a good seal between pipe and nozzle and on the other to prevent the pipe from detaching from the nozzle when pulled.

For such pipe clamps, a plastic clamp can be used for example, of polyamide for example such as Rilsan®. This type of plastic clamp, also sometimes called Serflex®, comprises a system of notches on a strip cooperating with a locking hook arranged in the head, such that the tightening is not reversible. In other words, after the strip is inserted into the head to form a loop, the strip is pulled to reduce the diameter of the loop and tighten the clamp; any return movement is prevented by the engagement of the hook in one of the notches of the strip. After tightening, to prevent the strip from projecting too far beyond the diameter of the clamp loop, the free portion of the strip is cut off close to the head of the clamp. The undetached remaining portion of the strip often has a sharp edge which can cut.

As an alternative to the plastic clamp, a metal clamp can be used which is in the form of a preformed ring having one or two "ears" projecting outward beyond the general shape of the ring of the clamp; this type of clamp is sometimes referred to as an Oetiker® clamp. After placement of the clamp on the pipe to be retained, a tool is used to crimp the ear (or ears) of the clamp which causes a permanent deformation and thus a narrowing of the major diameter of the ring and as a result tightens the clamp on the pipe. This type of clamping with a metal ring is particularly robust and reliable. However, at the point where the ear was crimped by the tool, there may be a burr or roughness which forms a sharp edge that can be damaging.

The metal clamp could also be a crimp-on earless metal clamp.

Whether plastic or metal, once such clamps are installed in biopharmaceutical assemblies, these assemblies may need to be transported or moved and there is therefore a risk of damage by the damaging parts of these clamps to other elements of the biopharmaceutical assembly, particularly the flexible bags or flexible pipes, which can cause a leakage or loss of sterilization that is detrimental to biopharmaceutical applications.

In addition, these clamps are easy to access (and thus can be removed) and do not allow guaranteeing a satisfactory image or aesthetics.

There is therefore a need to propose an improvement intended to at least partially overcome the above drawbacks of the known prior art.

OBJECTS AND SUMMARY OF THE INVENTION

A description of the invention as characterized in the claims is provided below.

According to a first aspect, the invention relates to a fluid-connection device adapted and intended for connecting a first wall defining a first fluid space, in the form of a flexible pipe, to a second wall defining a second fluid space, in the form of a pipe or enclosure that is flexible or semi-rigid and disposable, for ensuring fluid communication between the first fluid space and the second fluid space, comprising:
    a first connector defining a first hollow passage, adapted and intended for connection to the first wall and in fluid communication with the first space,
    the first connector comprising a tubular nozzle adapted and intended for receiving the pipe by insertion along the axis A,
    a pipe clamp adapted and intended for placement around the end of the pipe in order to clamp said pipe onto the tubular nozzle of the first connector,
    a protective cover forming a separate part, suitable for being snap-fitted into an operative position in which said cover is at least partially surrounding the first connector and its pipe clamp, the protective cover being snap-fitted into place in any orientation about axis A after the clamp is tightened,
    by means of which the pipe clamp cannot come into direct contact with external elements.

This prevents possible damage to the flexible bags or pipes adjacent to a damaging portion of the pipe clamp. In addition, it is possible to use a standard protective cover for a variety of different types of first connector, whether this first connector is intended to be welded to a bag or intended to interface with a second connector.

One will further note that insertion of the clamp does not require a specific orientation about an axis, which makes this operation relatively easy for an operator to perform, even if the operator is wearing aseptic protective equipment such as gloves, hairnet, goggles, etc.

In one embodiment, the protective cover is formed by two half-portions configured to come together around the clamp in the radial direction. It is thus advantageously possible to procure and install the protective cover after the pipe has been inserted onto the nozzle.

In one embodiment, the protective cover comprises two complementary semi-cylindrical portions connected by a flexible hinge portion, the two portions being adapted to snap-fit together in an area diametrically opposite the hinge area. Thus, the protective cover is advantageously obtained integrally in a single molding operation, and in addition its installation is particularly easy.

In one embodiment, the protective cover comprises flexible radial tabs intended to bear against the flexible pipe in an area between the position of the clamp and the front end of the pipe, such that radial pressure can be exerted by the flexible radial tabs to maintain the protective cover in its position radially and to a certain extent along the axis by friction.

In one embodiment, the protective cover comprises radial walls to enclose the pipe clamp and thereby immobilize or limit movement of the cover in the axial direction. In this manner the clamp is used as a positioning element for the protective cover with no need for another form of the first connector.

In one embodiment, the protective cover is a single part that is rotationally symmetrical, the protective cover being placed in an inoperative rearward position on the pipe prior to insertion of the pipe onto the tubular nozzle, then moved axially forward into an operative position where it covers the pipe clamp. In this manner it is sufficient to check the axial position of the cover to ensure that the clamp is protected. As the cover has been placed in an inoperative position on the pipe, this streamlines the assembly process; it is also conceivable to automate the installation of the protective cover.

In one embodiment, the protective cover comprises a front portion adapted to be snap-fitted onto a collar of the first connector when the protective cover is in the operative position on the clamp. It is thus possible to secure the position of the protective cover in its operative position on the collar between a shoulder and a clip of the cover.

In one embodiment, the protective cover comprises a rear portion adapted to bear against the pipe adjacent to the end of the nozzle of the connector when the cover is in the operative position. This prevents the entrance of foreign bodies between the pipe and the protective cover, and provides complementary retention of the protective cover in its operative position.

In one embodiment, the device further comprises a second connector defining a second hollow passage, adapted and intended for connection to the second wall and in fluid communication with the second space, the first connector and the second connector being adapted and intended to be coupled together in a relative coupling position along axis A, and the protective cover being suitable for snap-fitting into place so as to at least partially surround the first connector and the second connector, forming an indicator of proper coupling. Proper installation of the protective cover then reflects proper coupling of the first and second connectors.

In one embodiment, the cover comprises an annular inner groove which, in the coupling position, forms a locking means immobilizing the adjacent collars that are respectively part of the first and second connectors. This has the effect of locking the first and second connectors in their coupling position by means of the installation of the protective cover, and thus improves the function of proper assembly indicator.

In one embodiment, the annular inner groove forms at least one tapered portion (having a trapezoidal cross-section) so as to exert an axial pressure on the collars, which tends to bring the two connectors together. This exploits the movement of snap-fitting the protective cover to complete, where applicable, the coupling insertion path of the first and second connectors.

In one embodiment, the second connector comprises at least one flexible tab suitable for snap-fitting onto a second collar of the first connector, thereby establishing a first locking in the coupling position prior to installation of the cover. In this manner, the coupling position of the two connectors is maintained prior to actual installation of the protective cover, regardless of the connection reaction force.

In one embodiment, the device may further comprise an identifier such as a barcode or RFID tag or color code provided on the protective cover or on the first connector. It is thus easy to access information concerning the flexible bag and/or the biopharmaceutical product contained therein, and facilitates the traceability process.

In one embodiment, the cover comprises an opening enabling verification of the presence of the clamp once the cover is installed, so that the correct position of the clamp can be verified even after installation of the protective cover.

According to a second aspect, the invention relates to a biopharmaceutical assembly comprising a fluid-connection device as described above.

According to a third aspect, the invention also provides a kit of parts comprising a first connector as described above, and a pipe clamp and protective cover as described above for attaching a flexible pipe to the first connector.

In addition, the invention relates to an assembly of the above parts into an assembled state with the pipe clamp protected by the protective cover.

BRIEF DESCRIPTION OF THE DRAWINGS

The figures in the drawings are now briefly described.

MORE DETAILED DESCRIPTION

A detailed account of several embodiments of the invention is provided below, accompanied by examples and with reference to the drawings.

Figure 1:
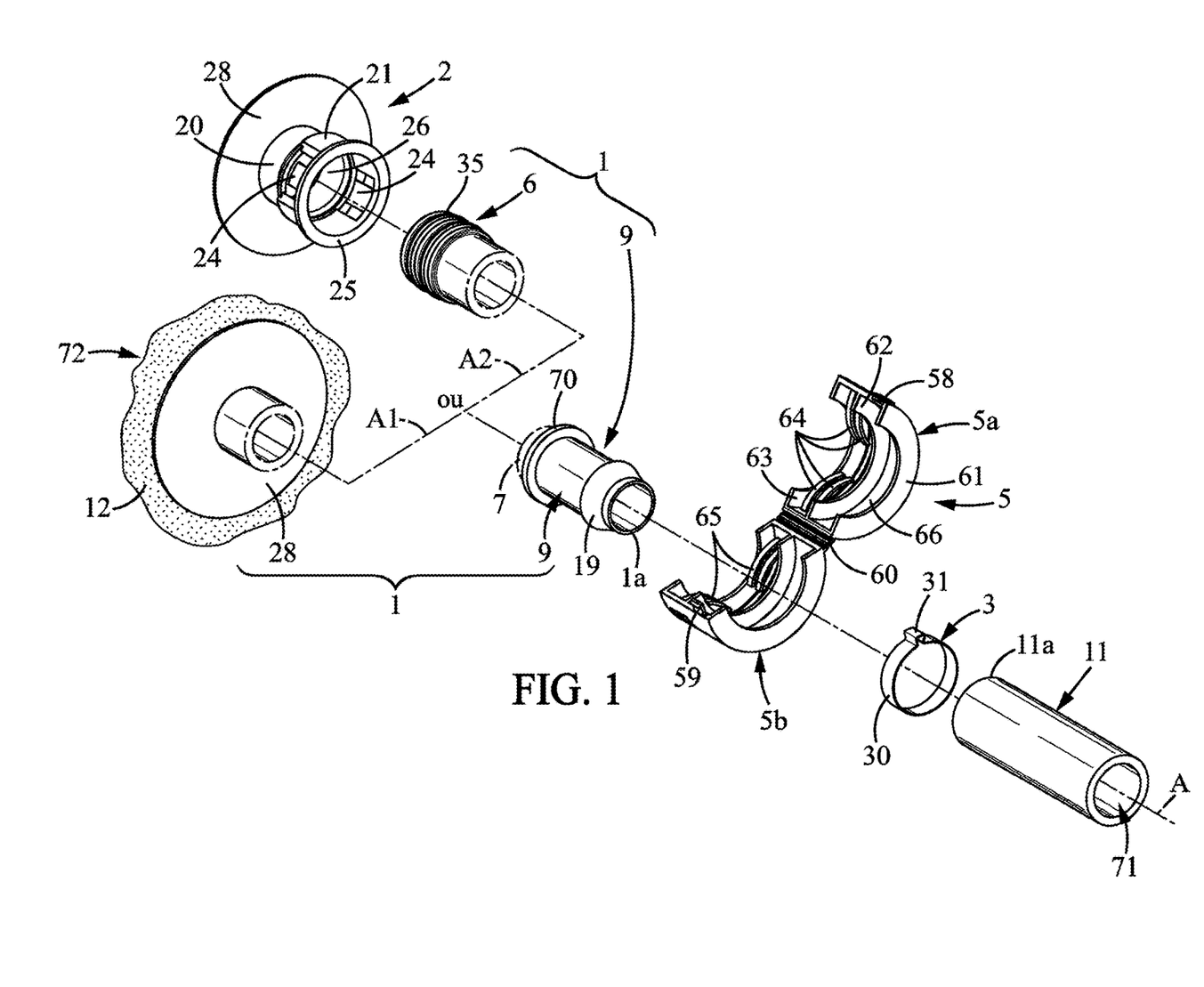
FIG. 1 is an exploded view of a connection device according to the invention, with a variant concerning the first connector which may be either (A1) a direct interface fixed to a bag or (A2) intended to interface with a second connector.
Figures 2, 3:
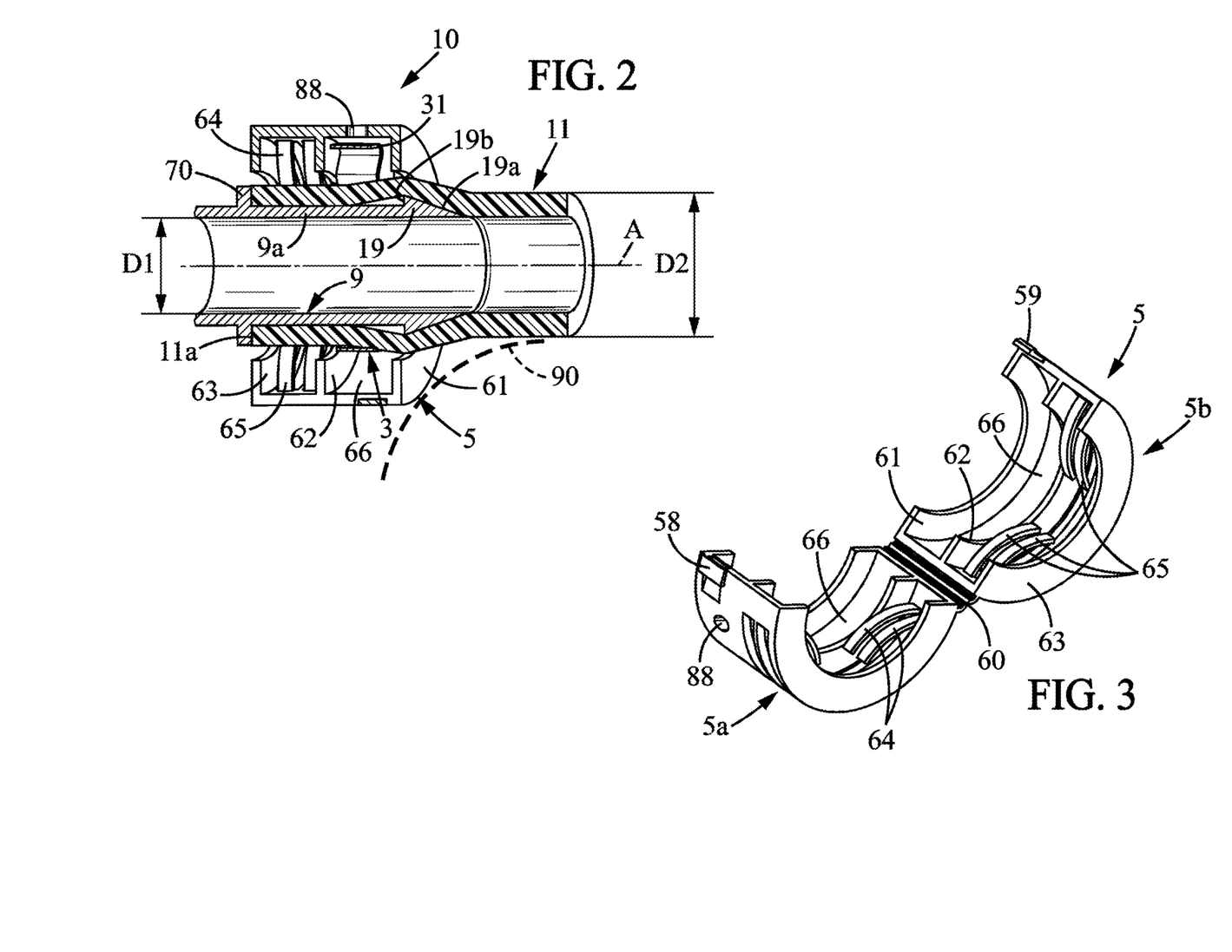
FIG. 2 is a partial axial sectional view of the connection device of FIG. 1, with the protective cover in the operative position.
FIG. 3 is a perspective view of the radial protective cover in the open position, seen from the opposite direction to the view in FIG. 1.

In the example illustrated in FIGS. 1-3, a flexible pipe 11 is connected to a first connector 1 in a fluidtight manner, by means of a pipe clamp 3 on a nozzle 9 of the pipe.

The first connector is intended to be coupled either directly (FIG. 1, variant A1) to a bag by means of an annular disc 28, or (FIG. 1, variant A2) to a second connector 2, in order to form a fluid connection between two fluid spaces 71,72.

The flexible pipe 11 can be generally defined as a first wall 11 defining a first fluid space 71.

The outside diameter of the flexible pipe 11 at rest is denoted D2, and one will note that the inside diameter D1 of the tubular nozzle 9 is substantially close to the inside diameter of the flexible pipe 11 at rest. However, several different types of pipe of different diameters can be used for insertion onto the nozzle 9.

The first connector 1 is made of synthetic material, more specifically it can be obtained by molding plastic material, for example polypropylene, polyethylene, polycarbonate, polysulfone, polyamide, PBT, or any other suitable plastic material.

According to variant A2, the first connector 1 comprises a tubular nozzle 9 at one end 1a, and an interface 6 for coupling with a second connector 2 at its other end. According to variant A1, the first connector 1 comprises an annular disc 28 for directly coupling with a bag.

The tubular nozzle 9 is rotationally symmetrical about axis A, and the same is true for the coupling interface 6. The coupling interface 6 is a male interface which is intended to be inserted into a female interface 2, described below. Of course, the reverse would be possible, meaning a male interface in the second connector and a female interface in the first connector. Genderless interfaces could also be used.

In the example shown, the male interface 6 in the first connector is generally cylindrical about A, with one or two outer grooves intended for receiving one or two O-rings 35.

The connector body 7 comprises, starting from the end of the nozzle 1a, a first ring-shaped collar 70 which serves as a stop for the insertion of the pipe. If the first connector has a coupling interface with the second connector, then a second collar 14 may be present, its usefulness to be discussed below.

The tubular nozzle 9 comprises an annular bead 19, which in the example illustrated has a slight ramp 19a on the side of the flexible pipe to be inserted and a shoulder 19b on the opposite side. The tubular nozzle may comprise a greater number of beads, for example such as the successive notches that are known per se.

When the flexible pipe 11 is threaded onto the tubular nozzle 9, the pipe is deformed radially outward by the ramp shape 19a, then progressively as it is inserted it returns to a narrower diameter at the cylindrical bearing surface 9a.

The insertion can continue until the front end of the pipe 11a comes to bear against said first collar 70 (see FIG. 2).

Once the flexible pipe is inserted onto the tubular nozzle 9, a pipe clamp 3 is placed around the pipe 3 at said bearing surface 9a. It should be noted here that the pipe clamp 3 may be arranged beforehand in a inoperative position around a rear portion of the pipe, prior to the insertion operation.

Once the clamp is in the appropriate position towards the collar 70 of the tubular nozzle, the clamp is tightened.

The pipe clamp represented in the figures is a metal clamp with only one ear 31 provided for tightening. There could be more than one ear, however.

Pliers are used, for example, to crimp the ear shape 31 so as to reduce the diameter of the ring 30 formed by the pipe clamp 3. The pipe clamp then has a smaller diameter than the outer surface of the flexible pipe at rest, and therefore exerts a radial force directed inward.

This radial pressure has two objectives: the first is to ensure a sufficiently effective seal between the pipe 11 and the tubular nozzle 9, and the second is to mechanically retain the pipe around the nozzle to prevent the pipe from detaching from the tubular nozzle if pulled, due to the aforementioned shoulder 19b.

Although a metal clamp with ear is represented, the clamp could be a plastic collar or a metal collar that is earless and crimped tight. In addition, there may be two clamps side by side.

According to variant A1, the first connector 1 comprises an attachment disc 28 for attaching to the flexible bag 12, such attachment usually being achieved by one or more welds 29 or by gluing. The disk 28 is flat and presses against a large surface area of the bag 12. The center of the disc 28 is open to provide fluid communication between the cylindrical inner space 82 of the second connector and the inner space 72 of the bag.

According to variant A2, the first connector 1 comprises a tubular region 20 forming the female coupling part and thus receiving said male interface 6; in the coupled position, said O-rings 35 are pressed inward by the cylindrical inner surface 26 of the tubular region 20 forming the female interface. A fluidtight fluid connection is thus obtained between the first connector 1 and the second connector 2.

In addition, the second connector 2 comprises a body 21 which extends from the tubular region 20 in a direction opposite the collar 28, possibly with snap-fitting tabs which will be detailed further below.

After installation of the clamp, a protective cover 5 is installed which has a definition suitable for variants A1 and A2, meaning regardless of the configuration of the connector on the side opposite the nozzle side.

The protective cover 5 is in the form of a part that is separate from the first connector. In the first embodiment, it is a radially inserted cover that can be procured and installed after the pipe has been inserted onto the nozzle.

Specifically, the protective cover is formed by two half-portions 5a, 5b configured to close onto one another in the radial direction, around the pipe clamp. Advantageously, the two half-portions are integrally formed by molding them as one piece, the two half-portions then being connected by a hinge area 60.

However, it is not excluded to have two half-portions that are provided separately.

One will note that the protective cover 5 can be moved into place radially from any direction: there is no particular orientation required about axis A.

The protective cover 5 is formed of plastic, for example of polypropylene, polyethylene, polycarbonate, polysulfone, polyamide, PBT, ABS.

Within the protective cover, a fairly wide internal groove 66 is provided for receiving the pipe clamp and in particular its radially projecting ear 31. This groove is flanked by two radial walls 61,62 which advantageously limit the axial movement of the cover after it has been installed in its operative position on the pipe clamp. Indeed, the central portion of the radial walls is almost in contact with the pipe, therefore they surround the body of the clamp and also the ear, and abut against said clamp in the event of axial movement of the protective cover.

In addition, the protective cover 5 comprises flexible radial tabs 64,65 provided to exert a radial inward pressure on the flexible pipe. The flexible radial tabs are positioned in front of the groove 66 so that the groove bears on the pipe in an area between the position of the collar and the front end of the pipe 11*a* (the first collar 70).

In addition, in a position diametrically opposite the hinge area 60, fastening means 58,59 are provided to maintain the two portions against one another. The fastening means 58,59 may take the form of a deformable clip or hook or any other form of engagement intended for the mutual retention of parts.

A third radial wall 63, opposite the first wall 61, makes it possible to close off the space between the pipe and the area covered by the protective cover, preventing objects or foreign bodies from entering the space inside the protective cover.

Once the protective cover is installed around the pipe and pipe clamp, damage by contact with a damaging portion of the clamp 3 can advantageously be avoided by the presence of the protective cover 5.

In particular, if the connection comes into contact with external elements 90, these can come into contact with the protective cover 5 but cannot come into direct contact with the pipe clamp 3, as is apparent in FIG. 2.

Although usually there is no indexing of the protective cover 5 to a particular angular position about the axis A, it would not be excluded to have an optional anti-rotation function for the cover 5. For this purpose, there could be a radial lug projecting from the first collar 70 and a plurality of corresponding notches in the third radial wall 63 (see FIG. 1). The cover 5 could then only be correctly closed around the connector 1 if the notch is aligned with a lug, at which point the cover is prevented from rotating about the axis A.

Figures 4A, 4B, 5:
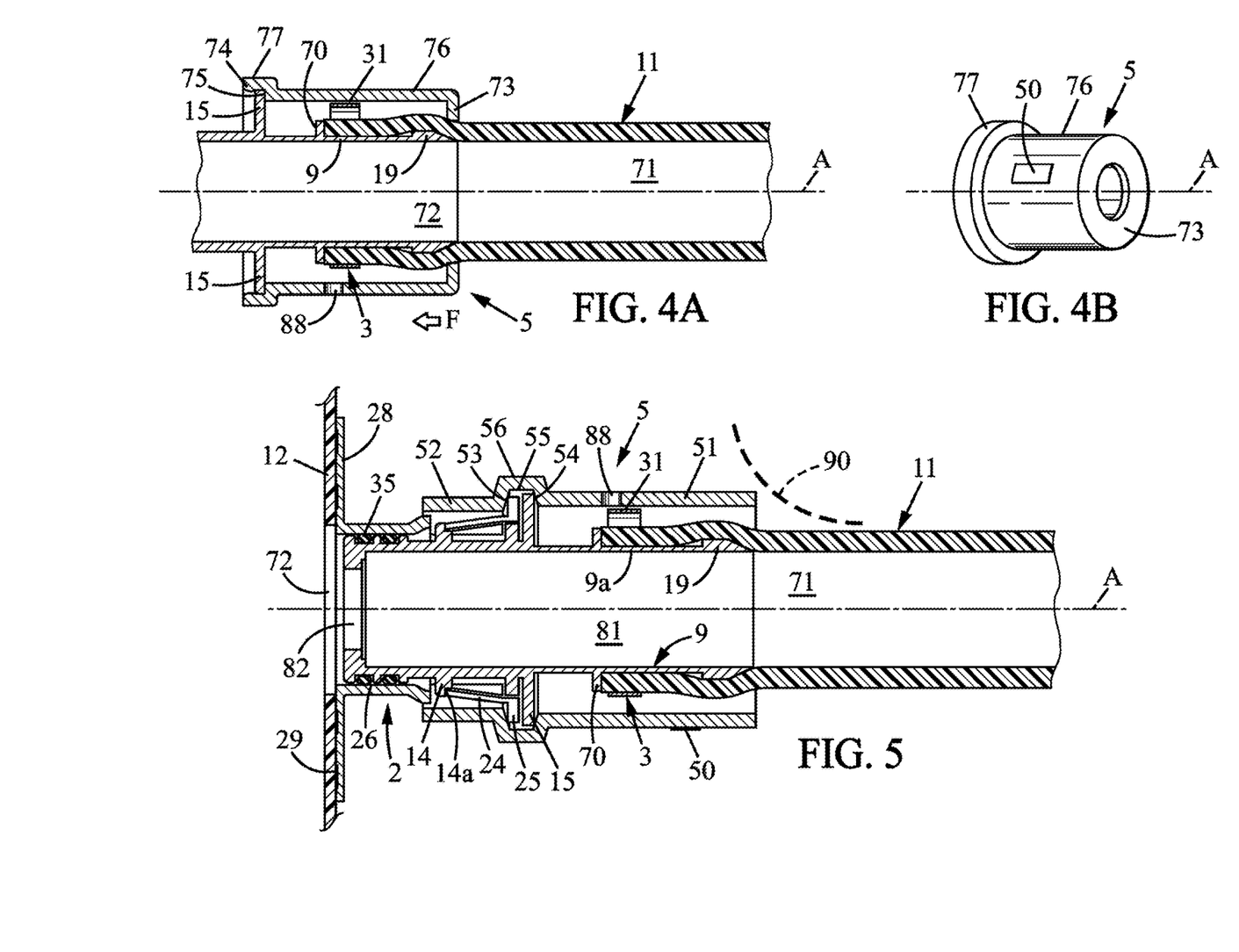
FIG. 4A is an axial sectional view of a connection device according to a second embodiment, with an axially displaceable protective cover.
FIG. 4B shows a perspective view of the protective cover of FIG. 4A.
FIG. 5 is an axial sectional view of a connection device according to a third embodiment in which the first connector interfaces with the second connector, with another embodiment of the protective cover.

In a second embodiment shown in FIGS. 4A and 4B, the protective cover 5 is in the form of a single part rotationally symmetrical around axis A, formed of a plastic material that is identical or similar to those already mentioned for the protective cover of the first embodiment.

In the illustrated example, the protective cover 5 comprises a cylindrical main portion 76 intended to be interposed, in the protective position, between the pipe clamp and an outer member 90. The protective cover 5 further comprises a front flange 77 located in front of the main portion in the direction of engagement of the cover (arrow F); said flange forms a radial shoulder 75 and comprises at least one flexible clip 74 on its front end.

The protective cover 5 is placed on the pipe in an inoperative position prior to assembling the device, in a rearward area relative to the front end of the pipe.

In addition to a first collar 70, the first connector comprises an annular main collar 15, of larger size than the first collar, positioned farther from the end 1*a* of the nozzle 9.

Once the flexible pipe has been inserted onto the nozzle and the pipe clamp has been installed and tightened, the protective cover is slid forward in the direction of the main collar 15.

Said radial shoulder 75 of the cover abuts against a face of the main collar 15.

Shaped clips 74 hook onto the other face of the main collar 15 in a manner that axially immobilizes the protective cover relative to the first connector 1.

In addition, the protective cover 5 may optionally have a rear radial annular wall 73 intended for isolating the internal space defined by the cover and the flexible pipe. The main collar 15 and this rear wall 73 thus prevent foreign bodies from entering the area covered by the cover.

In this second embodiment, there is no indexing of the protective cover to a particular angular position about the axis A; however, an anti-rotation function similar to what was described above for the first embodiment could also be provided.

In a third embodiment shown in FIG. 5, the first connector is intended to interface with the second connector 2 similarly to what has already been described above, the second connector also comprising a main collar 25 having a diameter identical or similar to that of the main collar 15 of the first connector 1.

According to an optional aspect represented in FIG. 5, when the first connector is intended to be coupled to the second connector, locking tabs 24 may be provided in the body of the second connector. These locking tabs 24, of which there are two in the example illustrated, are flexible, are moved apart when the first collar 14 reaches their free end, and then return inward to be positioned against a withdrawal-preventing abutment 14*a* on the rear of the first collar 14. It is then impossible to reverse the movement, or in other words to withdraw the first connector from the second connector, without first somehow eliminating the locking tabs 24.

In this third embodiment, the protective cover 5 is of the radial insertion type, formed in two half-portions that are closed onto one another as mentioned above for the first embodiment, without the protective cover 5 being indexed to any particular angular position about the axis A.

Advantageously, the cover comprises a radially external annular projection 56 having a corresponding internal annular groove 55 adapted to form, in the coupling position, a lock immobilizing the adjacent collars 15,25 against one another as can be seen in FIG. 5. Correct installation of the protective cover 5 provides an indication of a properly positioned coupling of the first and second connectors.

In addition, this internal groove 55 may comprise at least one tapered portion 53,54 (having a trapezoidal cross-section) so as to exert an axial pressure on the collars, which tends to bring the two connectors together, which can provide extra locking for the snap-fitting effect of said flexible tab 24.

Additionally, to facilitate the motion of closing the two half-portions of the cover onto the collars, the radially external rear portion of the collars may comprise a chamfer to facilitate sliding the tapered portions 53,54 into place.

In addition, the protective cover 5 may be such that it forms protective elements for the pipe clamp 3 on the first connector 1.

More specifically, the protective cover comprises a first axial extension 51 on the side of the first connector and a second axial extension 52 on the side of the second connector.

The first axial extension 51 forms a protection for the pipe clamp 3: in the coupling position, the clamp is located inside the inner region defined by this axial extension 51. In this manner, although the connection device may come into contact with external elements 90 during handling or movement of the device, it is not the pipe clamp which will come into contact with said external elements 90 but rather it will be the protective cover 5, in the current case the axial extension 51, which will come into contact with the one or more external elements 90 (see FIG. 5).

Thus, damage by contact with a damaging portion of the clamp 3 can advantageously be avoided.

If the second connector is connected to a second flexible pipe, the same features and advantages are obtained, mutatis mutandis, for the second connector concerning the pipe clamp clamping the second pipe on the nozzle of the second connector, and in this case the protective cover may advantageously be symmetrical relative to the interface plane of the collars 15,25.

Note that the first connector 1 defines a first hollow passage 81 intended to be placed in fluid communication with the first space 71. Similarly, the second connector defines the second hollow passage 82 already mentioned, intended to be placed in fluid communication with the second space 72 (the interior of the plastic bag in the specific case illustrated).

According to one optional feature, the connection device 10 may comprise an anti-rotation feature to prevent the first connector from rotating relative to the second connector about the axis A. More specifically, this could be for example a radial lug (not shown) arranged on the first connector, for example at the main collar 15 or alternatively at the first collar 14.

This lug would be received in a notch formed in the collar 25 of the second connector or in the body 21 of the second connector.

In addition, in all embodiments, a through-hole 88 (in other words an opening) may be provided in the body of the cover to allow visually verifying the presence of the clamp even once the cover has been installed. Of course, the hole can be of a different size, and there may be a plurality of holes about the body of the cover.

In addition, an optional feature compatible with all variants mentioned above is provided: this concerns the integration of an identifier 50, such as a barcode or electronic tag, for example an RFID tag, or even a color code. Preferably, this identifier is provided on the protective cover which is easily accessible from the outside. In the RFID solution, the identifier could be in any part of the first connector.

The invention claimed is:

1. A fluid-connection device adapted and intended for connecting a first wall defining a first fluid space, in the form of a flexible pipe, to a second wall defining a second fluid space, in the form of a pipe or enclosure that is flexible or rigid and disposable, in a biopharmaceutical assembly, for ensuring fluid communication between the first fluid space and the second fluid space, the fluid-connection device comprising:
   a first connector defining a first hollow passage, adapted and intended for connection to the first wall and in fluid communication with the first space, the first connector comprising a tubular nozzle adapted and intended for receiving the pipe by insertion along an axis (A),
   a pipe clamp adapted and intended for placement around the end of the pipe, with the tubular nozzle inserted within the end of the pipe, in order to clamp the end of said pipe onto the tubular nozzle of the first connector,
   a protective cover forming a separate part, suitable for being snap-fitted into an operative position in which said protective cover is at least partially surrounding the first connector and the pipe clamp, the protective cover being snap-fitted into place in any orientation about the axis (A) after the pipe clamp is tightened around the end of the pipe, with the tubular nozzle inserted within the end of the pipe, clamping the end of said pipe onto the tubular nozzle, wherein, with the protective cover snap-fitted into the operative position with the protective cover at least partially surrounding the first connector and the pipe clamp tightened around the end of the pipe clamping the end of the pipe onto the tubular nozzle, the protective cover protects the pipe clamp from coming into direct contact with elements that are in contact with an external side of the protective cover, and wherein the protective cover comprises flexible radial tabs intended to bear against the flexible pipe in an area between the operative position of the clamp and the front end of the pipe.

2. The device according to claim 1, wherein the protective cover is formed by two half-portions configured to come together around the clamp in the radial direction.

3. The device according to claim 2, wherein the protective cover comprises two complementary semi-cylindrical portions connected by a flexible hinge portion, and the two portions are adapted to snap-fit together in an area diametrically opposite the hinge area.

4. The device according to claim 3, wherein the cover comprises an opening enabling verification of the presence of the clamp once the cover is installed.

5. The device according to claim 2, wherein the protective cover comprises radial walls to enclose the pipe clamp and thereby immobilize or limit movement of the cover in the axial direction.

6. The device according to claim 5, wherein the cover comprises an opening enabling verification of the presence of the clamp once the cover is installed.

7. The device according to claim 2, wherein the cover comprises an opening enabling verification of the presence of the clamp once the cover is installed.

8. The device according to claim 1, further comprising a second connector defining a second hollow passage, adapted and intended for connection to the second wall and in fluid communication with the second space, the first connector and the second connector being adapted and intended to be coupled together in a relative coupling position along the axis (A), and the protective cover being suitable for snap-fitting into place so as to at least partially surround the first connector and second connector, forming an indicator of proper coupling.

9. The device according to claim 8, wherein the cover comprises an annular inner groove which, in the coupling position, forms a locking means immobilizing the adjacent collars that are respectively part of the first and second connectors, forming an indicator of proper assembly.

10. The device according to claim 8, wherein the inner groove forms at least one tapered portion so as to exert an axial pressure on the collars, which tends to bring the two connectors together.

11. The device according to claim 8, wherein the second connector comprises at least one flexible tab suitable for snap-fitting onto a second collar of the first connector, thereby establishing a first locking in the coupling position prior to installation of the protective cover.

12. The device according to claim 1, wherein the cover comprises an opening enabling verification of the presence of the clamp once the cover is installed.

13. The device according to claim 1, wherein the cover comprises an opening enabling verification of the presence of the clamp once the cover is installed.

14. The device according to claim 1, wherein, with the protective cover snap-fitted into the operative position with the protective cover at least partially surrounding the first connector and the pipe clamp tightened around the end of the pipe clamping the end of the pipe onto the tubular nozzle, the protective cover is located between the pipe clamp and the elements that are in contact with the external side of the protective cover thereby preventing the elements that are in contact with the external side of the protective cover from coming into direct contact with the pipe clamp.

15. A Biopharmaceutical assembly comprising a fluid-connection device according to claim 1.

* * * * *